United States Patent [19]

Oscarsson

[11] Patent Number: 4,660,802
[45] Date of Patent: Apr. 28, 1987

[54] LIQUID FLOW CONTROL DEVICE

[75] Inventor: Rolf A. Oscarsson, Hudson, Ohio

[73] Assignee: RAO Medical Devices, Inc., Hudson, Ohio

[21] Appl. No.: 796,316

[22] Filed: Nov. 8, 1985

[51] Int. Cl.[4] ............................................. F16L 55/14
[52] U.S. Cl. ........................................ 251/9; 251/230; 251/231; 251/251; 251/286; 251/904; 74/533
[58] Field of Search ................. 251/4, 9, 95, 101, 230, 251/231, 251, 904, 304, 312, 286; 74/533

[56] References Cited

U.S. PATENT DOCUMENTS

| | | | |
|---|---|---|---|
| 124,941 | 3/1872 | Egeberg et al. | 74/533 |
| 173,975 | 2/1876 | Lewis | 74/533 |
| 1,631,109 | 5/1927 | Hitzemann | 251/230 |
| 2,009,907 | 7/1935 | Teuber | 251/9 |
| 2,412,397 | 12/1946 | Harper | 251/251 |
| 2,832,562 | 4/1958 | Myers | 251/312 |
| 3,350,057 | 10/1967 | Luckenbill | 251/312 |
| 3,508,464 | 4/1970 | Kruchowy et al. | 251/230 |
| 3,940,107 | 2/1976 | Allenbaugh, Jr. | 251/297 |
| 4,078,763 | 3/1978 | Yamamoto | 251/286 |
| 4,129,231 | 12/1978 | Larson | 251/9 |
| 4,147,184 | 4/1979 | Jess | 251/312 |
| 4,568,061 | 2/1986 | Rabe | 251/315 |
| 4,570,901 | 2/1986 | Holtgraver | 251/297 |

Primary Examiner—Martin P. Schwadron
Assistant Examiner—Sheri M. Novack
Attorney, Agent, or Firm—Body, Vickers & Daniels

[57] ABSTRACT

A device for controlling the flow of a liquid medium passed therethrough comprises a cup-shaped plastic body member having a bottom end wall with a bore opening and a side wall forming with the bottom end wall a chamber through which the liquid medium is passed. A plastic stem member is journaled in the bore opening of the body member to rotatably mount the stem member thereon. The stem member overlies and closes off the open top end of the chamber and has a flow control element located within the chamber for controlling the flow rate of the liquid medium therethrough, as determined by the selected relative rotative position of the member. The stem member is snap-locked in assembled relation with the body member, and the two members are provided with actuating arm means including a radially outward projecting lever arm on the stem member for rotating the members relative to one another. Retaining means comprising a detent on the lever arm in ratcheting engagement with an arcuate ratchet bar on the body member are provided for maintaining the members in a selected relative rotative flow controlling position. In a tubing clamp form of the flow controlling device affording drop-by-drop liquid flow, the body member is provided with an open ended channelway thereacross open at its top for sidewise insertion of a compressible tubing therein and retention therein by the stem member on its snap-locked assembly with the body member. A flow control element in the form of a disc cam on the stem member engages with the tubing in the channelway on relative rotative movement of the body and stem members from an inoperative position in which the cam is disengaged from the tubing to an operative position in which the cam is engaged with the tubing to effect either partial or complete occlusion of the tubing, depending on the relative rotative position of the body and stem members.

28 Claims, 10 Drawing Figures

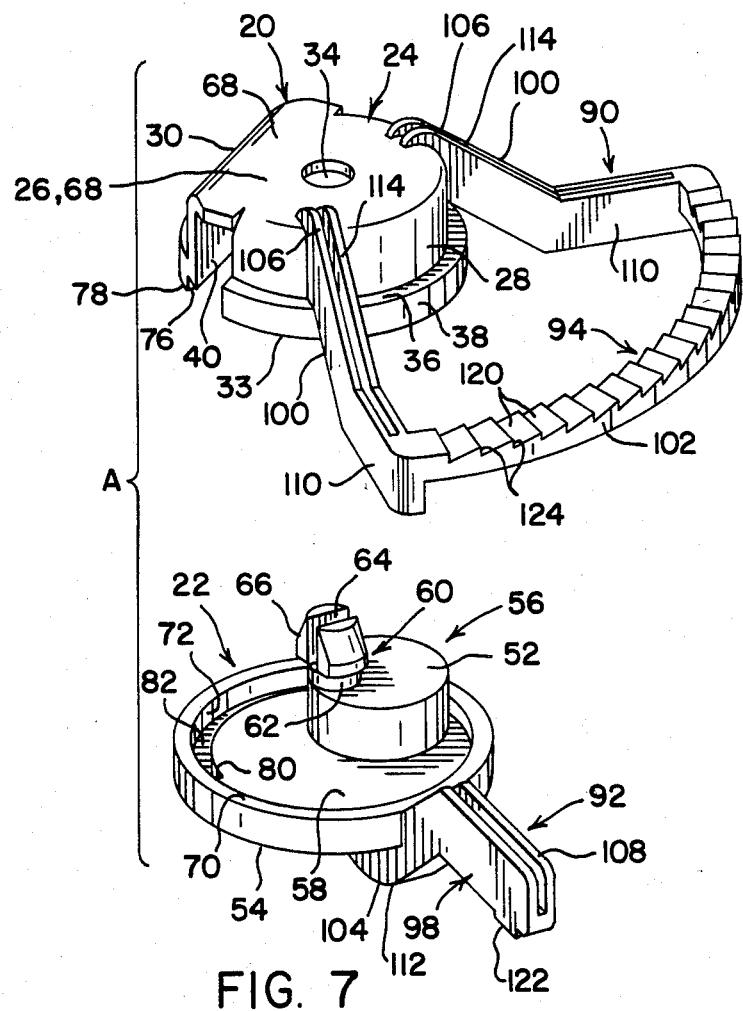
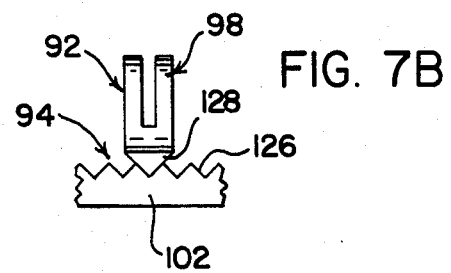
FIG. 7
FIG. 7B

LIQUID FLOW CONTROL DEVICE

This invention relates in general to a device for controlling the rate of flow of a liquid medium therethrough and, in one form of the invention, to a tubing clamp for controlling the rate of flow of a liquid medium through an elastically compressible tubing.

BACKGROUND OF THE INVENTION

There are many instances where the flow of a liquid medium through relatively small diameter pliable plastic tubing systems is regulated by the incorporation in the tubing system of a flow control device of comparatively small size and light in weight so that the device is capable of being supported or suspended in place solely by the tubing itself. In the medical field, for example, such type flow control devices are commonly employed to regulate the flow of medical fluids through intravascular catheter systems which customarily employ elastically deformable or compressible plastic tubing such as that commercially known as Tygon tubing and which are conventionally used for various medical purposes such as, for example, blood dialysis, clinical monitoring of a patient's blood system, or infusion of various medical fluids into a patient's venous system.

The flow control devices heretofore employed for such purposes generally have been either of complicated construction difficult to fabricate and/or assemble, or particularly in the case where employed in intravascular catheter systems, have necessitated in some circumstances the involved and inconvenient procedure of disconnecting the tubing at one or the other of its ends from either the catheter or supply of medical fluid, then inserting the free end of the elastically deformable plastic tubing endwise into and through the flow control device, and finally reconnecting the free end of the tubing to the catheter or to the supply of medical fluid.

The prior type flow control devices as referred to above, moreover, and more particularly those for regulating the flow of the liquid medium to a certain number of drops per given time unit, generally have not been provided with any so-called memory device for indicating the adjusted setting of the device that provided the desired flow rate of the liquid medium through the tubing system. As a result, when such prior flow control devices were disconnected from the tubing system for some reason or another, for instance, to check the reason for a stoppage of the liquid flow through the tubing system, it then became necessary to manually readjust the setting of the device, generally by trial and error procedure, in order to restore the previous setting of the device so as to provide the same rate of flow of the liquid medium through the tubing as before. Obviously, such a resetting procedure constitutes a time consuming operation and therefore an undesirable characteristic of the prior type fluid flow control devices such as used for medical purposes.

SUMMARY OF THE INVENTION

The present invention contemplates a new and improved liquid flow control device of the above described type which overcomes all of the above referred to problems and others and provides a device of such type which is of simple and inexpensive construction having flow controlling members snap-locked together in assembled rotative relation to each other and having effective retaining means for positively maintaining the flow controlling members in a selected rotative position.

Briefly stated, in accordance with one aspect of the invention, a liquid flow control device of the general type referred to above is comprised of molded plastic stem and body members which are snap-locked together in assembled rotative relation and have actuating arms with interengaged locking means for retaining the members in the desired selective rotative flow controlling positions relative to one another.

In accordance with a further aspect of the invention, the stem member is provided with a flow controlling element which extends into a chamber in the body member through which the liquid passes and which is provided with a projecting diametrically slotted journal bearing end portion which is adapted to be contractably insertable into and journaled in a bore opening in the body member for rotatively mounting and snap-locking the stem and body members together in assembled rotative relation.

In accordance with a still further aspect of the invention, the rotatably mounted stem and body members are provided with respective actuating arm means extending generally radially outward from the members for rotating them to the desired selective flow controlling relative position, and the actuating arm means on the body member is comprised of a pair of support arms interconnected at their outer ends by an arcuate ratchet bar with which the actuating arm means on the stem member is in ratcheting engagement to maintain the members in the selective rotative relative position.

According to still another aspect of the invention, in a tubing clamp form of flow controlling device embodying the invention the body member of the device is provided with an open ended channelway which opens outwardly of the open top end of the chamber in the body member for sidewise insertion of an elastically compressible tubing into the channelway and retention therein by the snap-locking of the stem member in assembled relation with the body member to closeoff the open top of the channelway.

In accordance with yet another aspect of the invention, the stem member of a tubing clamp as referred to above is provided with a flow control element in the form of a projecting cam portion extending into the chamber of the body member and engageable with an elastically deformable tubing in the channelway of the body member to compress the tubing on rotative movement of the stem member in one angular direction about the body member, and the cam member is formed with a projecting journal bearing end portion extending into and journaled in a bore opening in the body member to rotatively mount the stem member on the body member.

The principal object of the invention is to provide a liquid medium flow control device of the type as referred to hereinabove which is of simple and easily fabricated inexpensive construction comprised of molded plastic body and stem members snap-locked together in rotative assembled relation.

Another object of the invention is to provide a liquid medium flow control device as referred to above having body and stem members relatively rotatable to selected flow controlling positions and provided with a retaining arrangement for maintaining the members in the selected rotative flow controlling position.

A further object of the invention is to provide a liquid medium flow control device having body and stem members relatively rotatable to selected flow controlling positions and provided with respective actuating arm means in ratcheting engagement with one another to maintain the members in a selected relative rotative position.

A still further object of the invention is to provide a tubing clamp for elastically compressible tubing which is adapted for quick and easy insertion of the tubing into the clamp.

Another object of the invention is to provide a tubing clamp for elastically compressible tubing which is adapted for sidewise insertion of the tubing into the clamp for compressive clamping therein.

Still another object of the invention is to provide a tubing clamp for elastically compressible tubing into which the tubing is inserted sidewise between two component members of the clamp and is retained in clamping position therebetween by the snap-locking together of the members in assembled relation.

A further object of the invention is to provide a tubing clamp for elastically compressible tubing which is operative to compress and constrict the tubing in the clamp at a progressively slower degree for equal extents of closure movement of the clamp.

A still further object of the invention is to provide a tubing clamp for elastically compressible tubing having body and stem members relatively rotatable to constrict the tubing and control the flow rate of the liquid medium therethrough and provided with respective actuating arm means in ratcheting engagement with one another to maintain the members in a selected relative rotative position.

Further objects and advantages of the invention will be apparent from the following detailed description of preferred species thereof and from the accompanying drawings.

BRIEF DESCRIPTION OF THE DRAWINGS

In the drawings:

FIG. 7 is an exploded perspective view of the body and stem members of the tubing clamp shown in position for assembly;

FIG. 7B is a fragmentary elevation view of the modified ratchet bar and engaged actuating arm of the tubing clamp;

DESCRIPTION OF THE PREFERRED EMBODIMENTS

Figure 1:
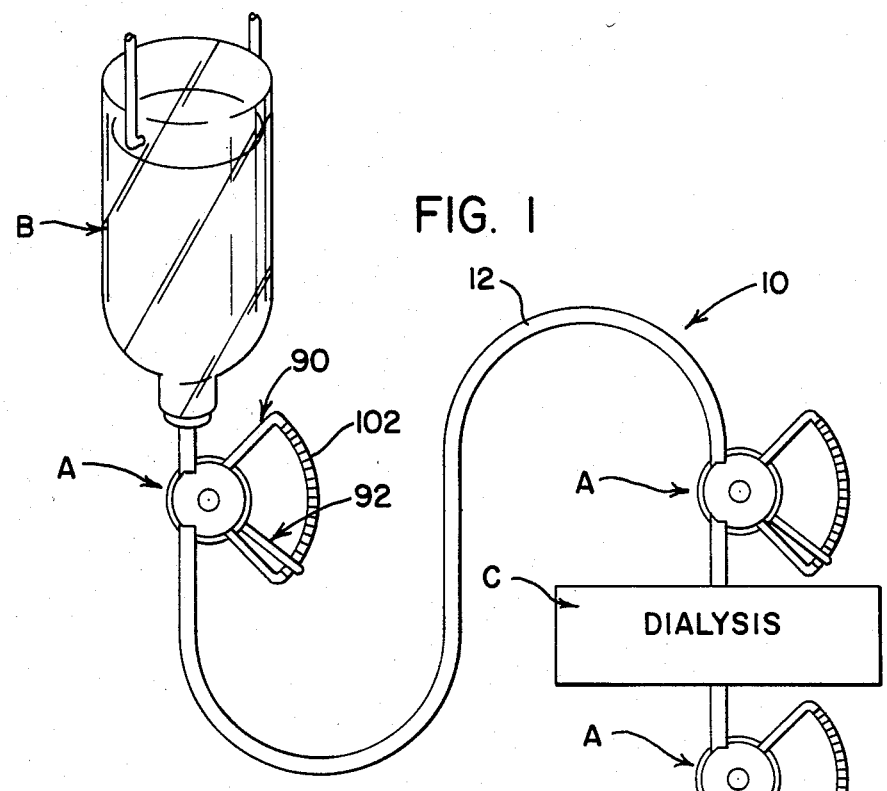
FIG. 1 is a schematic illustration of a blood dialysis system which includes flow control devices comprising the invention.
Figure 2:
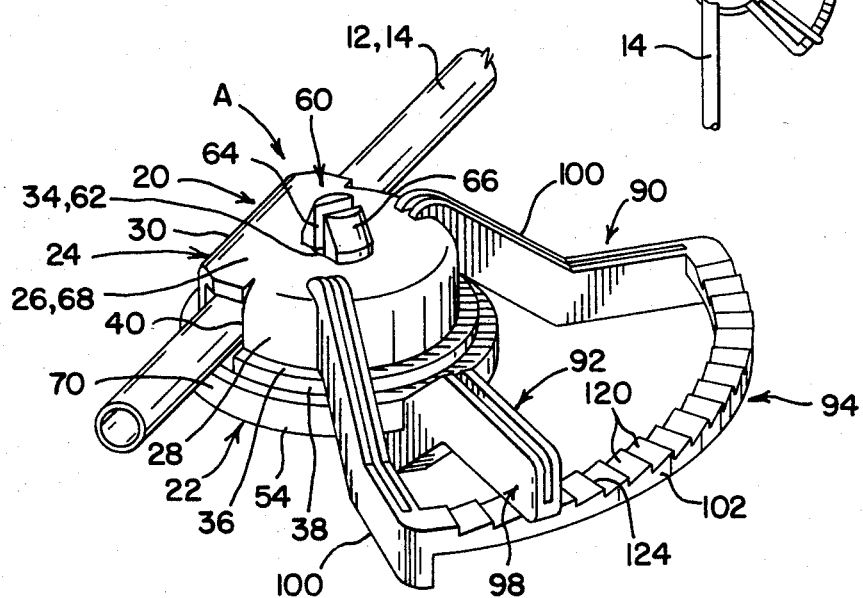
FIG. 2 is a perspective view on an enlarged scale of a tubing clamp form of flow control devices according to the invention.

Referring now to the drawings wherein the showings are for the purposes of illustrating a preferred embodiment of the invention only and not for the purpose of limiting same, the figures show the invention as embodied in a tubing clamp form A of a liquid medium flow control device according to the invention. It is to be understood however, that the invention may be utilized in other types of fluid flow control devices such as, for example, metering valves, medical flushing units for catheter systems, and similar devices wherever it may be found to have suitable utility therefor.

By way of example, the fluid flow control device A is shown as incorporated in a catheter system generally designated 10 for blood dialysis purposes and including a tubing section 12 connecting a supply of a medical fluid in a container B through a pair of the control devices A to a dialysis unit C, and a similar tubing section 14 connecting the dialysis unit C through a control device A to a catheter (not shown) inserted into an artery or vein of a patient. The tubing sections 12 and 14 are comprised of elastically compressible plastic tubing such as the plastic tubing commercially known as Tygon tubing commonly employed in catheter systems generally. The tubing sections 12 and 14 are inserted and clamped in the respective tubing clamps A which, in the operation of the catheter system 10, are adjusted to compress and occlude the elastic tubing in the respective clamps A to the extent necessary to provide the desired rate of flow of the fluid or blood, e.g. drops per unit time interval, through the respective tubing sections 12, 14.

The tubing clamps A according to the invention are each comprised, in general, of an assembly of two separate molded plastic members, i.e., a body member 20 and a stem member 22 which, after positioning of the tubing 12 or 14 therebetween, are adapted to be snap-locked together in assembled relation to thereby retain the tubing section in position in the clamp assembly A for clamping therein. Body member 20 is comprised of a cup-shaped portion 24 having a flat bottom end wall 26 and an upstanding side wall 28 of cylindrical contour except for a straight chordal-extending portion 30 at one side thereof. The end wall 26 and side wall 28 together define a chamber 32 which is open at the top end 33 of the cup portion 24. End wall 26 is provided with a centrally located circular bore opening 34 therethrough coaxial with the axis of the cylindrical portion of the side wall 28 and serving as a journal bearing for rotatably mounting the stem member 22 on the body member 20. At its open top end, the side wall 28 is provided with a radially outward extending peripherial lip portion 36 having a cylindrical outer surface 38 concentric with the axis of the bore opening 34 to serve as an additional journal bearing support for rotatably mounting the stem member 22 on the body member 20.

The cup-shaped portion 24 of the body member 20 is provided with an open ended channelway 40 extending transversely thereacross in a chordal direction through the cylindrical side wall 28 and laterally offset to one side of the bore opening 34 in the bottom end wall 26. The channelway 40 opens outwardly of the open top end 33 of the cup member 24 to permit sidewise insertion of the tubing 12 or 14 thereinto, and it is formed by opposed notches 42, 44 in the side wall 36 which notches extend from the open top end 33 of the cup portion 24 to the bottom end wall 26 thereof. The laterally outward side of the channelway 40 is formed by the straight chordal extending portion 30 of the side wall 28. The laterally inward side of the channelway 40 is formed by the side edges of the notches 42, 44 in the wall portion 28 and additionally by a short wall portion 46 extending a short distance inwardly into the chamber 32 from the cylindrical side wall 28 in parallel relation to the chordal outward side 30 of the channelway 40. The inwardly extending wall portion 46 terminates at its inward end 48 an appreciable distance from the opposite portion of the side wall 28 of the cup portion 24 so as to leave a substantial sidewise opening 50 of the channelway 40 into the chamber 32 for movement therethrough into clamping engagement with the tubing 12 or 14 positioned in the channelway 40 of a flow control element 52 on stem member 22.

The stem member 22 of the tubing clamp A is comprised of a flat circular cap portion 54 having a stem portion 56 projecting inwardly from the inner face 58 of the cap portion and comprised of the flow control element 52 and a diametrically slotted journal end portion 60 projecting endwise from the flow control element 52 and axially aligned with the axis of the circular cap portion 54. The journal end portion 60 is formed with a circular journal portion 62 immediately adjacent the flow control element 52 for extending into and journaling in the bore opening 34 of the body member 24, when the body and stem members 20, 24 are in assembled relation, to thereby rotatably mount the stem member 20 on the body member 24. The journal end portion 60 is further provided with a diametrical slot 64 and with a tapered head end 66 of enlarged size relative to the journal portion 62 in a direction normal to the slot 64. The provision of the diametrical slot 64 in the journal end portion 60 enables the spring contraction thereof into, and the passage thereof through the bore opening 34 in the body member 22 so as to engage and snap-lock behind the outer face 68 of the bottom end wall 26 of the body member to thereby hold the stem member 22 in assembled rotative relation with the body member, with the flat inner face 58 of the cap portion 54 held against the top end 33 of the side wall 28 of the body member 20.

The circular cap portion 54 of stem member 22 is provided therearound with an inwardly extending peripheral lip 70 having a circular inner wall 72 concentric with the axis of the cap portion for rotative bearing engagement with the cylindrical outer surface 38 of the lip portion 36 on body member 20 to thereby provide an additional rotative support of the stem member on the body member. When the stem member 22 is snap-locked in assembled relation with the body member 20, the cap portion 54 of the stem member then overlies and completely covers or closes the open top of the channelway 40 in the body member so as to trap and retain in the channelway any tubing 12 or 14 previously placed therein for clamping in the tubing clamp A.

Figure 5:
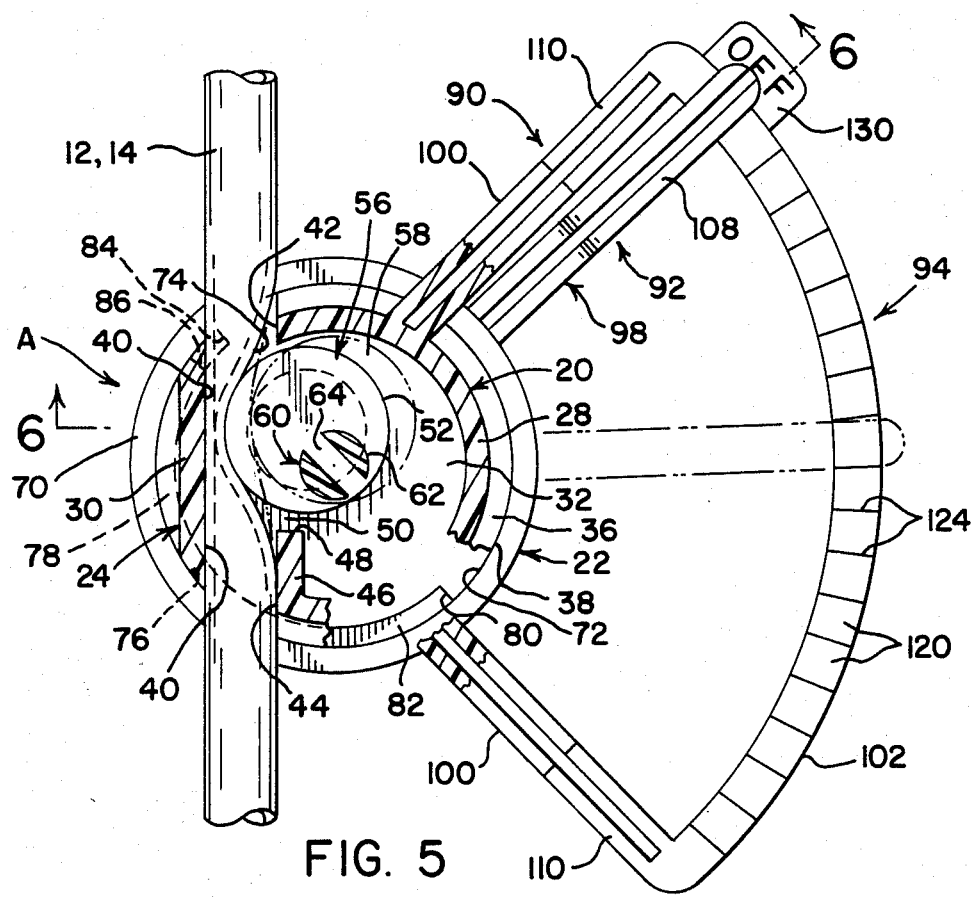
FIG. 5 is a plan view similar to FIG. 3 and partly in section but showing the tubing clamp in its fully closed or off position pinching and closing off the tubing therein.
Figure 6:
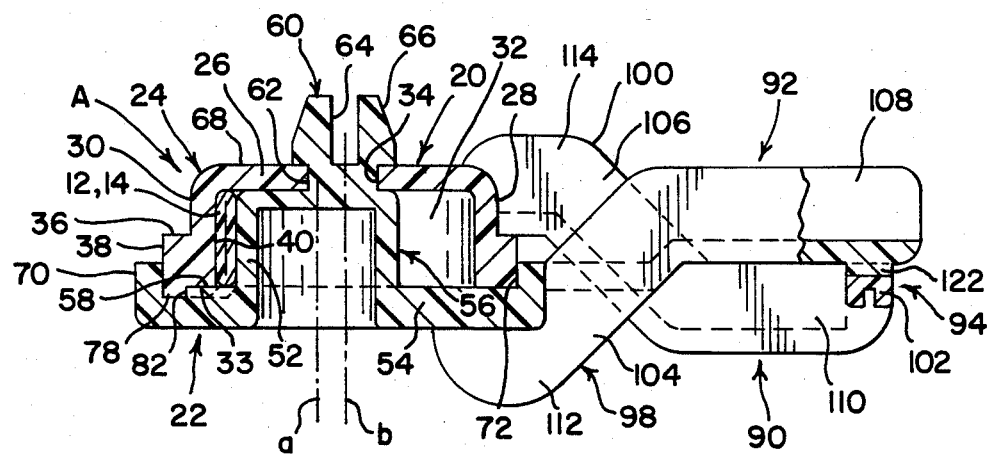
FIG. 6 is a sectional view on the line 6—6 of FIG. 5.

The flow control element 52 on the stem member 22 of the tubing clamp A is in the form of a cylindrical cam portion projecting inwardly from the inner face 58 of the cap portion 54 with its axis a (FIG. 3) offset from the axis b of the journal portion 62 of stem member 22 so as to be eccentrically located thereon. In the assembled position of the body and stem members 20, 22, the circular cam 52 is located at a position within the chamber 32 of body member 20 directly opposite or alongside the sidewise opening 50 of the channelway 40 into the chamber so as to move through the opening 50 into clamping engagement with the tubing 12 or 14 present in the channelway, on rotative movement of the body and stem members 20 and 22 relative to one another in one direction. Thus, on counterclockwise rotative movement of the stem member 22 relative to the body member 20 in FIGS. 3 and 5 from its inoperative to its operative position, the cam portion 52 is moved from the dotted line inoperative position thereof shown in FIG. 3 disengaged from the tubing 12 or 14 in the channelway 40 to its fully clamped position as shown in solid lines in FIG. 5 so as to compress and contract the tubing 12 or 14 in the passageway 40 against the chordal back wall 30 thereof, in the manner as indicated at 74 in FIG. 5, to a flattened and completely occluded condition as shown in FIGS. 5 and 6.

The inoperative relative rotative position of the body and stem members 20, 22 is determined by the engagement of one end 76 of a raised arcuate rim portion 78 of limited angular extent on the open top end 33 of the body member 20 with one end 80 of an arcuate groove 82 formed in and extending part way around the periphery of the inner face 58 of the cap portion 54, within which groove 82 the raised rim portion 78 slidably fits and rotatively moves during the rotative movement of the body and stem members 20, 22 relative to one another. The operative relative rotative position of the body and stem members 20, 22 varies in accordance with the degree to which the tubing 12 or 14 present in the channelway is to be compressed and contracted by cam portion 52. The limiting operative relative rotative position of the body and stem members 20, 22, however, is determined by the wall thickness of the particular tubing 12 or 14 present in the channelway 40 and the extent of relative rotative movement of the members 20, 22 required to compress and contract the tubing to a flattened and completely occluded condition as shown in FIGS. 5 and 6. To assure such complete flattening and full occluding of whatever wall thickness tubing 12 or 14 is present in channelway 40, the arcuate groove 82 in cap portion 54 is formed of an arcuate length such that the other or front end 84 of the groove will be spaced a slight distance from the back end 86 of the raised rim portion 78 a sufficient distance to permit the required extent of relative rotative movement of the members 20, 22 to assure the complete flattening of the tubing 12 or 14 in each case. Preferably, however, the arcuate groove 82 in cap portion 54 is formed of an arcuate length such as to locate the front end 84 thereof at an angular position around the axis of rotation of members 20, 22 where it will be engaged by the back end 86 of the raised rim portion 78 on body member 20, where no tubing is present in channelway 40, just before the cam portion 52 of stem member 22 would otherwise engage with and bind against the straight chordal back wall portion 30 of the channelway 40 with resulting possible breakage or other damage to various parts of the device A.

It will be obvious that the body and stem members 20, 22 may be rotated relative to one another, during the usage of the device A, only to a partial degree of the full arcuate extent of relative rotative movement thereof required to completely flatten the tubing 12 or 14, in order to thereby compress and contract the tubing 12 or 14 in the channelway 40 only to a partial extent so as to retard the flow of the fluid through the tubing to a selected rate such as, for example, a given number of drops of the fluid per minute or other unit time interval.

The stem and body members 20, 22 are provided with respective actuating arm means 90 and 92 for effecting the relative rotative movement of the members 20, 22 to the selected flow controlling position and which also provides retaining means 94 for maintaining the members 20, 22 in the selected flow controlling rotative position. In this connection, such a retaining means 94 is necessary in order to prevent the rotative return of the body and stem members 20, 22 from their selected flow controlling position to their original starting position by the counterforce exerted by the compressed elastic tubing 12 or 14 against the cam portion 52 of the stem member 22.

The actuating arm means 92 on the stem member 22 comprises a single lever arm 98 extending generally radially outward from the circular cap portion 54 of the stem member. Similarly, the actuating arm means 90 on the body member 20 comprises a pair of support arms 100 also extending generally radially outward from the body member 20 on opposite sides of the lever arm 98 and angularly spaced apart around the body member a distance corresponding approximately to the extent of angular relative rotative movement of the members 20, 22 required to move them from their inoperative position to their operative position in which the tubing 12 or 14 in the channelway 40 is fully compressed to a flattened, completely occluded condition. The pair of support arms 100 are interconnected at their outer ends by an arcuate bar portion 102 centered on the turning axis of the members 20, 22.

Figure 4:
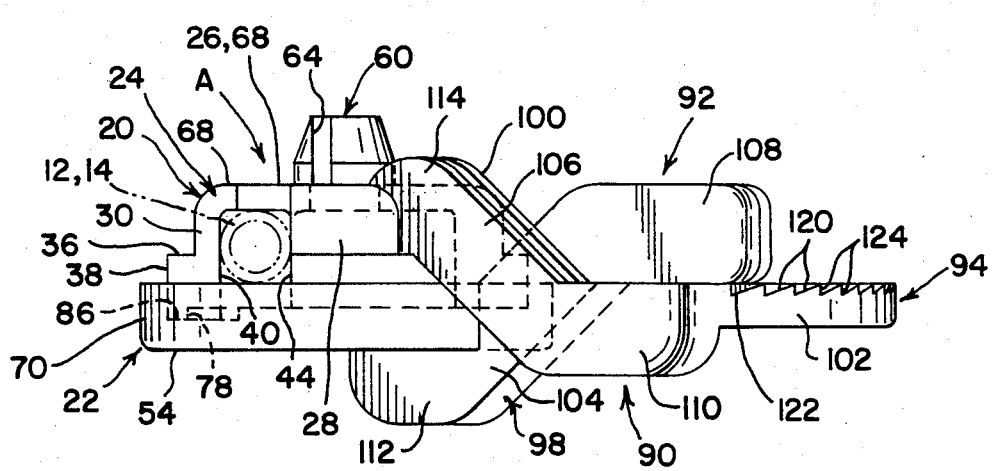
FIG. 4 is an elevation view of the tubing clamp shown in FIG. 3.

As shown in FIGS. 4 and 6, at least one of the single lever arm 98 or the pair of support arms 100, and preferably both thereof as illustrated, is or are offset intermediate their ends in opposite directions axially of the turning axis of the members 20, 22, as indicated at 104 and 106 respectively, so that the lever arm 98 extends through the space between the support arms 100 and the arcuate bar portion 102 and overlaps the pair of support arms 100, with the offset outer end portions 108 and 110 of the lever arm 98 and the pair of support arms 100 respectively located on opposite axial sides of each other from the axial sides on which the inner end portions 112, 114 of the arms 98 and 100 are located. In the assembled position of the body and stem members 20, 22, the offset outer end portion 108 of the lever arm 98 extends across and engages with the arcuate connecting bar portion 102 of the actuating means 90, and it is slightly deflected axially of the turning axis of the members 20, 22 so as to have a slight degree of spring pressure engagement with the arcuate bar portion 102.

The retaining means 94 for maintaining the body and stem members 20, 22 in their selected relative rotative flow controlling position is comprised of a series of ratchet teeth 120 located on and along substantially the full arcuate extent of that axial side of the arcuate connecting bar portion 102 engaged by the lever arm 98, and a detent 122 (FIG. 7) located on the outer end of the lever arm and engaging with the ratchet teeth 120 to lock the members 20 and 22 in place against return rotative movement to their inoperative relative position. To this end, the locking faces 124 of the ratchet teeth 120 lie in respective axial planes which include the turning axis of the members 20, 22 and which face opposite the direction of return rotative movement of the stem member 22 relative to the base member 20 to the inoperative or starting rotative position of these members. When the base and stem members 20, 22 are rotatively moved relative to one another by the manual operation of their respective actuating arm means 100, 98 in a direction to set the members in a selected flow controlling position, the detent 122 on the lever arm 98 in ratcheting engagement with the ratchet teeth 120 rides over the successive ratchet teeth and catches behind the locking face 124 of that ratchet tooth located at the selected rotative position of the stem member 22 relative to the body member 20, thus locking these members in the selected flow controlling position.

The members 20, 22 may be freed from their locked rotative position simply by spring deflecting the lever arm 98 and holding it out of ratcheting engagement with the ratchet teeth 120 on the arcuate ratchet bar 102 whereupon the lever arm 98 and associated stem member 22 may then be returned to the original inoperative starting rotative position relative to the body member by the manual manipulation of the lever arm 98 aided by the force of the compressed elastic tubing 12 or 14 in the channelway 40 acting to effect such return rotative movement of the members 20, 22 to their inoperative position. If desired, a suitable indicator or marking may be placed on the arcuate ratchet bar 102 to denote the setting of the lever arm 98 on the ratchet bar for the selected flow controlling position of the members 20, 22. If it should be necessary for some reason or other to disassemble the members 20, 22 to permit the removal of the tubing 12 or 14 therefrom, this may be readily accomplished simply by suitably squeezing the projecting slotted journal end portion 60 of the stem member 22 as by means of a pair of pliers, for example, to contract such end portion 60 the necessary amount for passage through the bore opening 34 in the body member 20, and then guiding the head end 66 of the contracted journal end portion 60 into the bore opening 34 whereupon the body and stem members 20, 22 may then be pulled apart and separated to free the tubing 12 or 14 in the channelway 40 for sidewise removal therefrom.

Instead of the ratcheting arrangement shown in FIG. 7 for locking the members 20, 22 in the selected relative rotative position and employing ratchet teeth 120 with axially extending locking faces 124, the arcuate ratchet bar 102 may be provided with V-section ratchet teeth 126 as shown in FIG. 7B and a detent 128 of corresponding V-section then provided on the actuating lever arm 98. Such a modified ratcheting arrangement enables easy rotative movement of the members 20, 22 in either relative direction due to the camming action of the engaged V-section ratchet teeth 126 and detent 128 to provide self-disengagement therebetween. This is of particular advantage during the rotative adjustment of the members 20, 22 relative to one another to achieve the desired selected flow controlling setting thereof.

Figure 3:
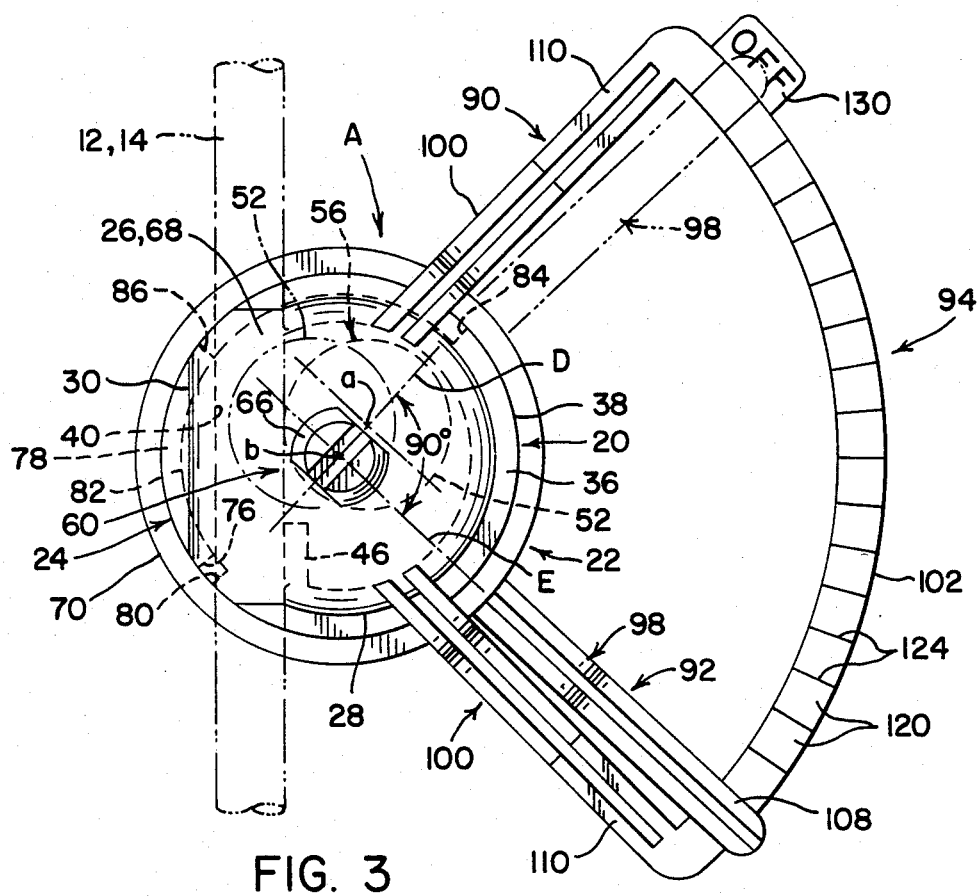
FIG. 3 is a plan view on an enlarged scale of the tubing clamp shown in FIG. 1 with an elastically deformable tubing in clamping position therein.
Figure 8:
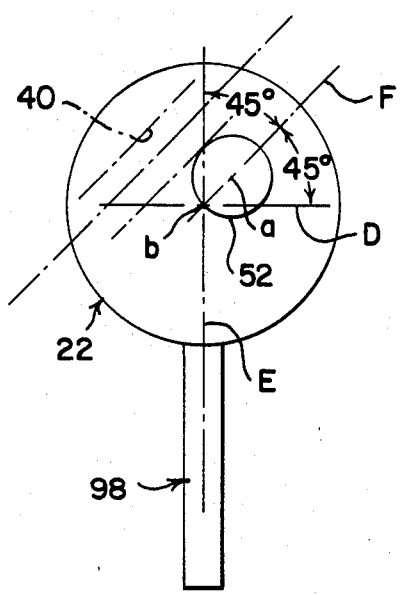
FIG. 8 is a schematic plan view of a modified form of the stem member of the tubing clamp; and, FIG. 9 is a graph showing the degree of occlusion of a tubing in a tubing clamp provided with the modified stem member of FIG. 8, in relation to the angle of closure movement of the actuating arm on the stem member of the tubing clamp.
Figure 9:
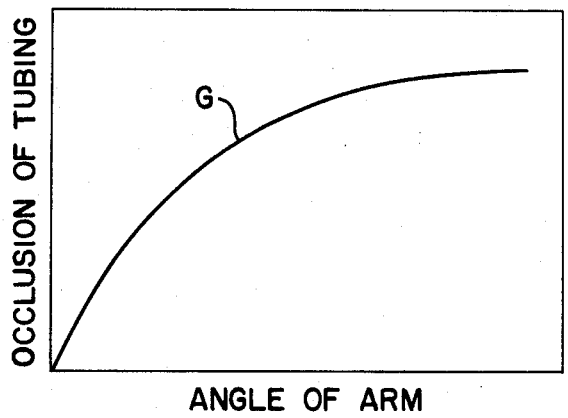

The modification shown in FIG. 8 illustrates a preferred form of the invention wherein the axis a of the disc cam portion 52 of stem member 22, in place of being located as shown in FIG. 3 in a radial plane D of the stem member extending at approximately 90° to the radial plane E of the stem member in which the lever arm 98 extends radially outward from the stem member, is located instead in a radial plane F of the stem member which extends at approximately 45° to the radial plane E of the stem member and approximately parallel to the channelway 40 in the assembled body and stem members when in their inoperative relative rotative position with the cam portion 52 disengaged from the tubing 12 or 14 in the channelway 40. Such a modified location of the cam portion 52 on stem member 22 then provides the desirable rate of occluding of the tube 12 or 14 by the cam portion 52 as shown by the curve G in the graph of FIG. 9, the occluding of the tubing being fastest at the start of the angular movement of the lever arm 98 and associated stem member 22 relative to the body member 20 in a direction to effect the occluding of the tubing and then proceeding at a progressively slower rate during the continued angular movement of the arm 98 and stem member 22 relative to the body member 20.

The arcuate ratchet bar 102 may be provided with an outwardly projecting indicator tab 130 carrying a suitable marking such as OFF to denote that the flow of fluid through the tubing 12 or 14 is shut off when the actuating lever arm 98 is set opposite the indicator tab 130.

Having thus described the invention, it is claimed:

1. A device for controlling the flow of a liquid passed therethrough, said device comprising a cup-shaped body member having a bottom end wall and a surrounding side wall together defining a chamber open at one end, a stem member rotatably mounted on said body member for rotative movement relative thereto about an axis of rotation, said stem member including a flow control element rotatable within said chamber about the said axis, and a projecting journal end portion on said flow control element extending through and journaled in a bore opening in the said bottom end wall of said body member and snap-locked therein to rotatively mount the stem member in place, said journal end portion being diametrically slotted to permit spring contraction thereof at its outward end to a smaller diametrical dimension across one of its diameters, and said journal end portion being provided around its outermost end with laterally outward projecting locking lip means of cam-shaped section for snap-locking behind the said bottom end wall of the body member, on insertion and passage of said journal end portion into and through the said bore opening in said bottom end wall, to thereby lock the said members together in assembled rotative relation.

2. A tubing clamp device as defined in claim 1 and further comprising actuating means on said members including a lever arm fixed on said stem member and projecting generally radially outward therefrom for effecting rotative movement of the stem member relative to said body member, and interengageable retaining means on said members to hold them in a selected rotative position relative to one another, said retaining means comprising detent means on said lever arm in ratcheting engagement with an arcuate ratchet bar on said body member, and said arcutate ratchet bar being provided with an outwardly projecting indicator tab carrying a marking denoting the flow controlling setting of the stem member relative to the body member when the said lever arm is located at a position along said ratchet bar opposite the said indicator tab.

3. A device for controlling the flow of a liquid passed therethrough and comprising a side insertion tubing clamp, said device comprising a body member of cup-shaped form having a bottom end wall with a bore opening therethrough and a surrounding said wall defining with said bottom end wall a chamber open at the top and within which the flow of said liquid is controlled, a stem member rotatably mounted on said body member for rotative movement relative thereto about an axis of rotation, said stem member including a flow control element rotatable within said chamber about the said axis, actuating means on said members including a lever arm on said stem member projecting generally radially outward therefrom for effecting rotative movement of the stem member relative to said body member, said body member also having an open ended channelway extending transversely thereacross through the said side wall and chamber and laterally offset to one side of said bore opening, said channelway opening sidewise into the said chamber toward the said bore opening and outwardly of the open top of said chamber for sidewise insertion into the open top of the channelway of an elastically compressible tubing to be clamped therein, said stem member being journaled in said bore opening and overlying and closing the said open top of said channelway to retain the said tubing in place therein, the said flow control element on said stem member comprising a disc cam located eccentrically thereon within the said chamber, with respect to the said axis of rotation of said members, and engageable with the tubing in said channelway through the said sidewise opening thereof, on rotation of the stem member relative to the body member from an inoperative position to an operative position, to thereby laterally compress and contract the tubing against the opposing side of the channelway, and interengageable retaining means on said members for maintaining them in a selected rotative position relative to one another, said retaining means comprising detent means on said lever arm in ratcheting engagement with an arcuate ratchet bar on said body member.

4. A tubing clamp as defined in claim 3, wherein the said arcuate ratchet bar is provided with an outwardly projecting indicator tab carrying a marking denoting the flow controlling setting of the stem member relative to the body member when the said lever arm is located at a position along said ratchet bar opposite the said indicator tab.

5. A side insertion tubing clamp comprising a cup-shaped body member having a bottom end wall with a bore opening therethrough and a surrounding side wall defining with said bottom end wall a chamber open at its top, said body member also having an open ended channelway extending transversely thereacross through the said side wall and chamber and laterally offset to one side of said bore opening, said channelway being open at the top of the body member for sidewise insertion of an elastically compressible tubing into the channelway through its said open top, a stem member rotatively mounted on said body member and having a cap portion overlying and closing the open top of said channelway along at least a portion of its length to retain the said tubing in place therein, said stem member having a stem portion projecting into said chamber from said cap portion and journaled in said bore opening, said stem portion including a disc cam within said chamber and engageable with the tubing in said channelway, through an opening in the side thereof, to laterally compress and contract the tubing on rotation of the stem member in one direction relative to the body member from an inoperative position to an operative position, and interengageable retaining means on said members to hold them in a selected rotative position relative to one another.

6. A tubing clamp as defined in claim 5, wherein the said stem member is snap-locked in place onto the said body member for rotation relative thereto in said bore opening.

7. A tubing clamp as defined in claim 6, wherein the said body and stem members are provided with respective actuating arm means extending generally radially outward from the said members.

8. A tubing clamp as defined in claim 7, wherein the said retaining means is comprised in part said actuating arm means.

9. A device as defined in claim 6, wherein one of said members is provided with an arcuate groove concentric with the said axis of rotation, and the other one of said members is provided with an arcuate rib concentric with said axis of rotation and received in and slidable within said arcuate groove during relative rotation of said members, said arcuate groove having an arcuate length substantially greater than the arcuate length of said arcuate rib, and the ends of said arcuate rib being engageable with the respective ends of said arcuate groove to confine the rotative movement of the said members in opposite directions relative to one another to respective limiting positions.

10. A tubing clamp as defined in claim 5, wherein the said stem portion is provided with a journal end portion projecting from said disc cam into and journaled in said bore opening to rotatively mount the stem member on said body member.

11. A tubing clamp as defined in claim 10, wherein the said body and stem members are provided with respective actuating arm means extending generally radially outward from the said members.

12. A tubing clamp as defined in claim 11, wherein the said retaining means is comprised in part of said actuating arm means.

13. A tubing clamp as defined in claim 5, wherein the said side wall of said body member is of cylindrical outer shape and the said bore opening is coaxial with said side wall, and said channelway extends in a chordal direction across and through the said cylindrical side wall of said body member.

14. A tubing clamp as defined in claim 13, wherein the said cap portion of said stem member is provided with an annular lip portion therearound coaxial with and engaging around and enclosing the open top end of said body member to further rotatively support the stem member in place thereon.

15. A tubing clamp as defined in claim 5, wherein the said body and stem members are provided with respective actuating arm means extending generally radially outward from the said members.

16. A tubing clamp as defined in claim 15, wherein the said retaining means is comprised in part of said actuating arm means.

17. A tubing clamp as defined in claim 15, wherein the said actuating arm means on one of said members comprises a pair of support arms spaced apart around the axis of relative rotation of said members, and the said actuating arm means on the other one of said members comprises a single lever arm extending between the said pair of support arms on said one member.

18. A tubing clamp as defined in claim 17, wherein the said pair of support arms are interconnected at their outward ends by an arcuate ratchet bar concentric with the axis of rotation of said members relative to one another, and the said single lever arm extends radially across the said arcuate ratchet bar in sliding engagement therewith and is provided with detent means in ratcheting engagement with said ratchet bar to form the said retaining means.

19. A tubing clamp as defined in claim 15, wherein the said body and stem members are provided with interengageable stop means for confining the rotative movement of the stem member in opposite directions relative to the body member to respective limiting positions.

20. A tubing clamp as defined in claim 18, wherein the said pair of support arms extend from the said body member and the said single lever arm extends from the said stem member.

21. A tubing clamp as defined in claim 15, wherein one of said stem and body members is provided with an arcuate rib concentric with the axis of rotation of said stem and body members and slidable within and engageable at its opposite ends with respective ends of an arcuate groove formed in the other one of said members and concentric with said axis of rotation to confine the rotative movement of the stem member in opposite directions relative to the body member to respective limiting positions.

22. A tubing clamp as defined in claim 21, wherein the said arcuate rib is provided on said body member and the said arcuate groove is provided in said stem member.

23. A tubing clamp as defined in claim 18, wherein at least one of either said single lever arm or said pair of support arms is axially offset intermediate its ends from one to the other axial side of the other one of said lever arm or said pair of support arms so that the lever arm extends outwardly between the said pair of support arms and its outer end portion is in ratcheting engagement with the other axial side of the said arcuate ratchet bar.

24. A tubing clamp as defined in claim 23, wherein each one said single lever arm and said pair of support arms is axially offset intermediate the ends thereof from one to the other of the axial sides of the other of said arms.

25. A tubing clamp as defined in claim 5, wherein the portion of said disc cam engageable with the said tubing in said channelway, on rotative movement of said stem member from its said inoperative position to its operative position, is of circularly arcuate shape approximately centered on an axis which, when said stem member is in its said inoperative position with the disc cam thereof disengaged from the said tubing in said channelway, lies in a plane approximately parallel to said channelway and including the axis of relative rotation of said body and stem members.

26. A device as defined in claim 5, wherein the said body and stem members are provided with interengageable stop means for confining the rotative movement of said members relative to one another to respective limiting positions.

27. A side insertion tubing clamp comprising a cup-shaped body member having a bottom end wall with a bore opening therethrough and a surrounding side wall defining with said bottom end wall a chamber open at its top, said body member also having an open ended channelway extending transversely thereacross through the said side wall and chamber and laterally offset to one side of said bore opening, said channelway being open at the top of the body member for sidewise insertion of an elastically compressible tubing into the channelway through its said open top, a stem member rotatively mounted on said body member and having a cap portion overlying and closing the open top of said channelway along at least a portion of its length to retain the said tubing in place therein, said stem member having a stem portion projecting into said chamber from said cap portion and provided with a projecting journal end portion extending into and journaled in said bore opening, said stem portion including a disc cam within said chamber and engageable with the tubing in said channelway, through an opening in the side thereof, to laterally compress and contract the tubing on rotation of the stem member in one direction relative to the body member from an inoperative position to an operative position, and interengageable retaining means on said members to hold them in a selected rotative position relative to one another, said journal end portion being diametrically slotted inwardly from its outward end for spring contraction thereof to a smaller diametrical dimension across one diameter and being provided around its outermost end with laterally outward projecting locking lip means of cam-shaped section for snap-locking behind the said bottom end wall of said body member, on insertion and passage of said journal end portion into and through the said bore opening, to thereby lock the said body and stem members together in assembled rotative relation.

28. A tubing clamp as defined in claim 27, wherein the said body and stem members are provided with respective actuating arm means extending generally radially outward from the said members.

* * * * *